(12) United States Patent
Hatano et al.

(10) Patent No.: US 10,918,266 B2
(45) Date of Patent: Feb. 16, 2021

(54) ENDOSCOPE

(71) Applicant: OLYMPUS CORPORATION, Tokyo (JP)

(72) Inventors: Keisuke Hatano, Koganei (JP); Shigeyasu Kishioka, Kunitachi (JP)

(73) Assignee: OLYMPUS CORPORATION, Tokyo (JP)

( * ) Notice: Subject to any disclaimer, the term of this patent is extended or adjusted under 35 U.S.C. 154(b) by 380 days.

(21) Appl. No.: 16/026,326

(22) Filed: Jul. 3, 2018

(65) Prior Publication Data

US 2018/0310803 A1 Nov. 1, 2018

Related U.S. Application Data

(63) Continuation of application No. PCT/JP2016/079061, filed on Sep. 30, 2016.

(30) Foreign Application Priority Data

Jan. 5, 2016 (JP) .................................. 2016-000576

(51) Int. Cl.
*A61B 1/005* (2006.01)
*A61B 34/00* (2016.01)
*A61B 90/00* (2016.01)

(52) U.S. Cl.
CPC ............ *A61B 1/0052* (2013.01); *A61B 34/74* (2016.02); *A61B 2034/742* (2016.02); *A61B 2090/034* (2016.02)

(58) Field of Classification Search
CPC ... A61B 1/00066; A61B 1/0052; A61B 34/20; A61B 34/25; A61B 34/30; A61B 34/37;
(Continued)

(56) References Cited

U.S. PATENT DOCUMENTS 9,743,827 B2* 8/2017 Yasunaga .............. A61B 1/0057
2004/0193014 A1* 9/2004 Miyagi .............. A61B 1/00039
600/146

(Continued)

FOREIGN PATENT DOCUMENTS

| JP | 2003-135385 A | 5/2003 |
|----|---------------|--------|
| JP | 2004-321612 A | 11/2004 |
| JP | 2014-26004 A | 2/2014 |

OTHER PUBLICATIONS

International Search Report dated Jan. 10, 2017 received in PCT/JP2016/079061.

*Primary Examiner* — Aaron B Fairchild
(74) *Attorney, Agent, or Firm* — Scully, Scott, Murphy & Presser, P.C.

(57) ABSTRACT

An operation lever type (joystick type) endoscope including an operation lever capable of adjusting a bending angle of a bending portion in response to a tilting operation of an operation portion, and an exterior cover an outer periphery portion of which is watertightly fixed to an operation portion body (an operation portion), and an inner periphery portion of which watertightly covers an outer circumference of the operation lever, the exterior cover being capable of deforming by pressure fluctuation inside the operation portion (that is, pressure fluctuation of a sealed space formed inside the endoscope), is provided with a restricting member 90 configured to restrict expansion of the exterior cover by the fluctuation of the internal pressure.

6 Claims, 9 Drawing Sheets

(58) Field of Classification Search
CPC ........... A61B 2017/00398; A61B 2017/00477; A61B 2034/301; G06F 3/0338
See application file for complete search history.

(56) References Cited

U.S. PATENT DOCUMENTS

| | | | |
|---|---|---|---|
| 2008/0275303 A1* | 11/2008 | Koitabashi | G05G 5/04 600/146 |
| 2016/0192823 A1* | 7/2016 | Yasunaga | A61B 1/0052 600/109 |
| 2017/0196435 A1* | 7/2017 | Sato | G02B 23/2476 |
| 2018/0325355 A1* | 11/2018 | Ito | A61B 1/00066 |

* cited by examiner

ENDOSCOPE

CROSS REFERENCE TO RELATED APPLICATION

This application is a continuation application of PCT/JP2016/079061 filed on Sep. 30, 2016 and claims benefit of Japanese Application No. 2016-000576 filed in Japan on Jan. 5, 2016, the entire contents of which are incorporated herein by this reference.

BACKGROUND OF THE INVENTION

1. Field of the Invention

The present invention relates to an endoscope that causes a bending portion to perform a bending operation in response to a tilting operation of an operation lever.

2. Description of the Related Art

Conventionally, in order to observe the inside of a subject or object that is difficult to observe, such as a part inside a body of a living body or inside a structure, an endoscope insertable into the subject or object is widely used, for example, in a medical field or an industrial field.

An insertion portion of such an endoscope is provided with a bending portion for improving insertability and observability inside the subject or object. The bending portion is operated for bending by a bending operation device provided on an operation portion.

As a bending operation device, a joystick type bending operation device for performing a bending operation of the bending portion by a tilting operation of an operation lever is widely known. In the joystick type bending operation device, in order to secure watertightness inside the endoscope, allowing the tilting operation of the operation lever projecting outside the operation portion, an outer side of the operation lever is watertightly covered with an exterior cover configured with an elastic member made of rubber or the like (see, for example, Japanese Patent Application Laid-Open Publication No. 2004-321612).

For the endoscope of this type, a leak test for determining whether the internal watertightness is secured or not is performed at the time of cleaning or the like after use. In general, the leak test is performed by applying positive pressure to the inside of the endoscope via a ventilation portion provided on the endoscope.

SUMMARY OF THE INVENTION

An endoscope according to one aspect of the present invention includes: an operation portion provided on a proximal end side of an insertion portion including a bending portion; an operation lever provided on the operation portion, the operation lever being capable of adjusting a bending angle of the bending portion in response to a tilting operation; a flexible exterior cover an outer periphery portion of which is watertightly fixed to the operation portion, and an inner periphery portion of which watertightly covers an outer side of the operation lever, the flexible exterior cover being capable of deforming by fluctuation of internal pressure of the operation portion; and a restricting member configured to restrict expansion of the exterior cover by the fluctuation of the internal pressure.

An endoscope according to another aspect of the present invention includes: an exterior cover forming a sealed space inside and being capable of deforming in response to internal pressure in the sealed space; an operation lever watertightly fixed to the exterior cover; and a restricting member provided on the operation lever, the restricting member configured to restrict expansion of the exterior cover by fluctuation of the internal pressure.

DETAILED DESCRIPTION OF THE PREFERRED EMBODIMENT

Figure 1:
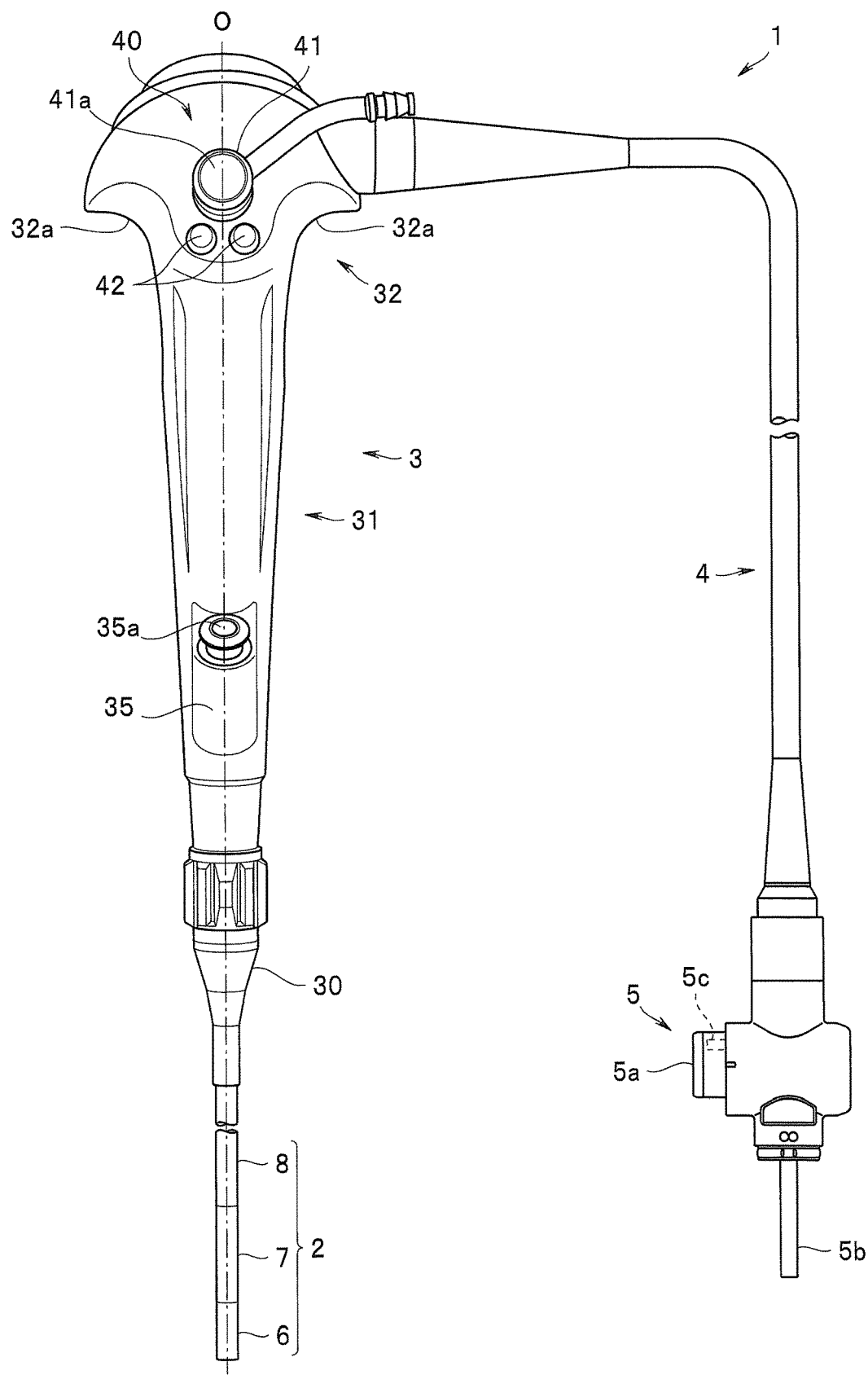
FIG. 1 is a front view showing an external appearance of an endoscope.
Figure 2:
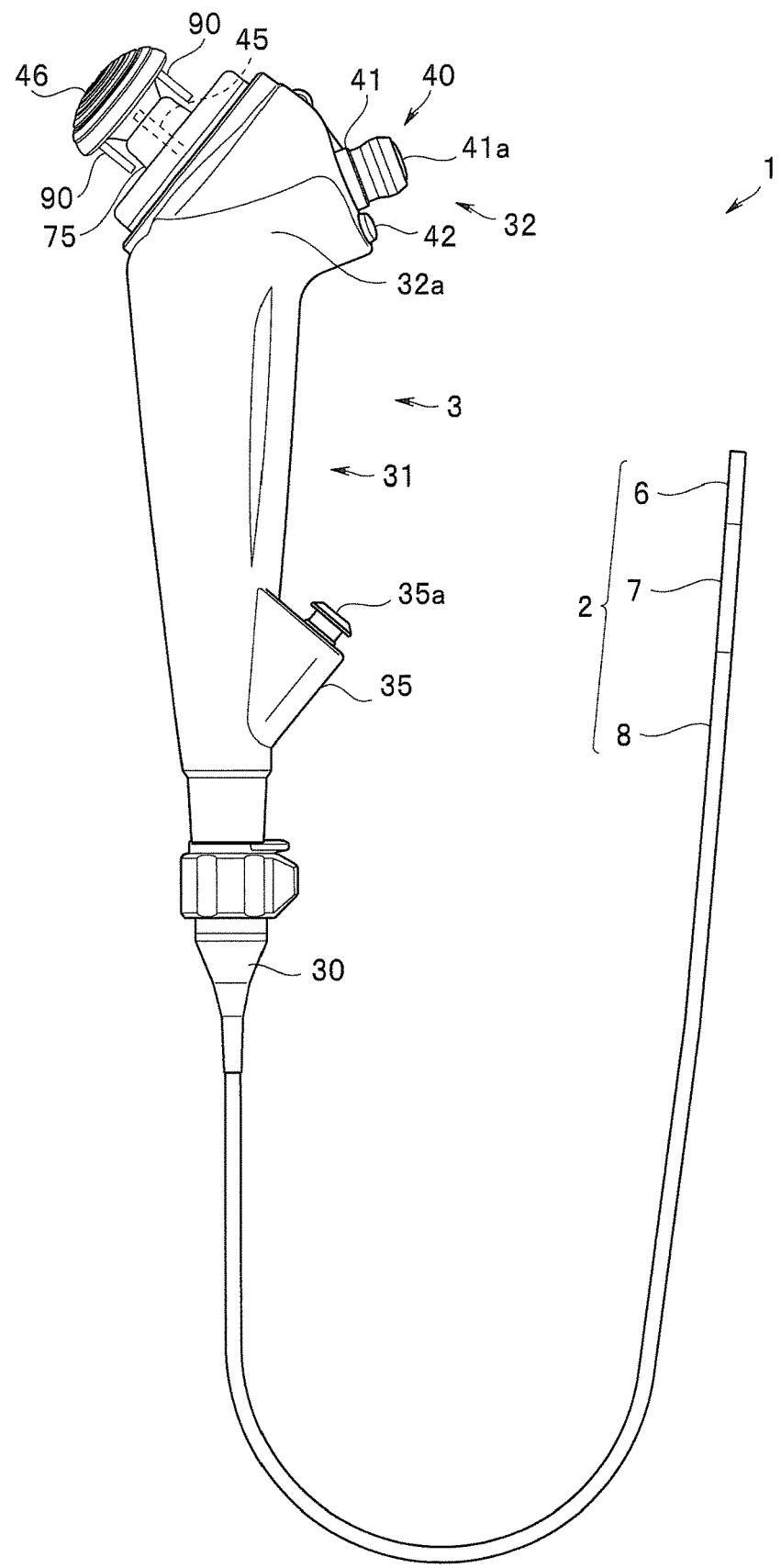
FIG. 2 is a right side view showing the external appearance of the endoscope.
Figure 3:
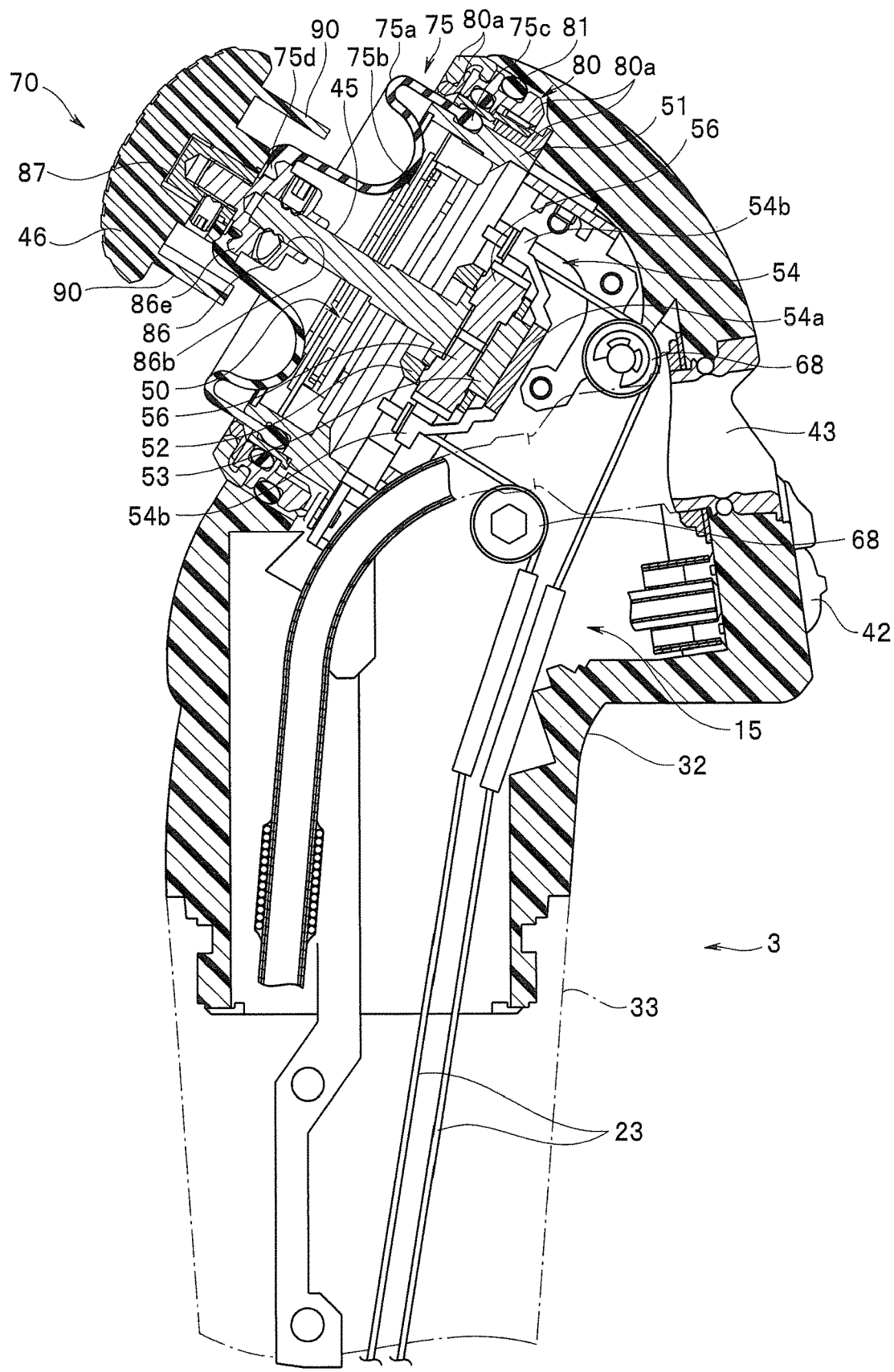
FIG. 3 is a sectional view of a main part of an operation portion.
Figure 4:
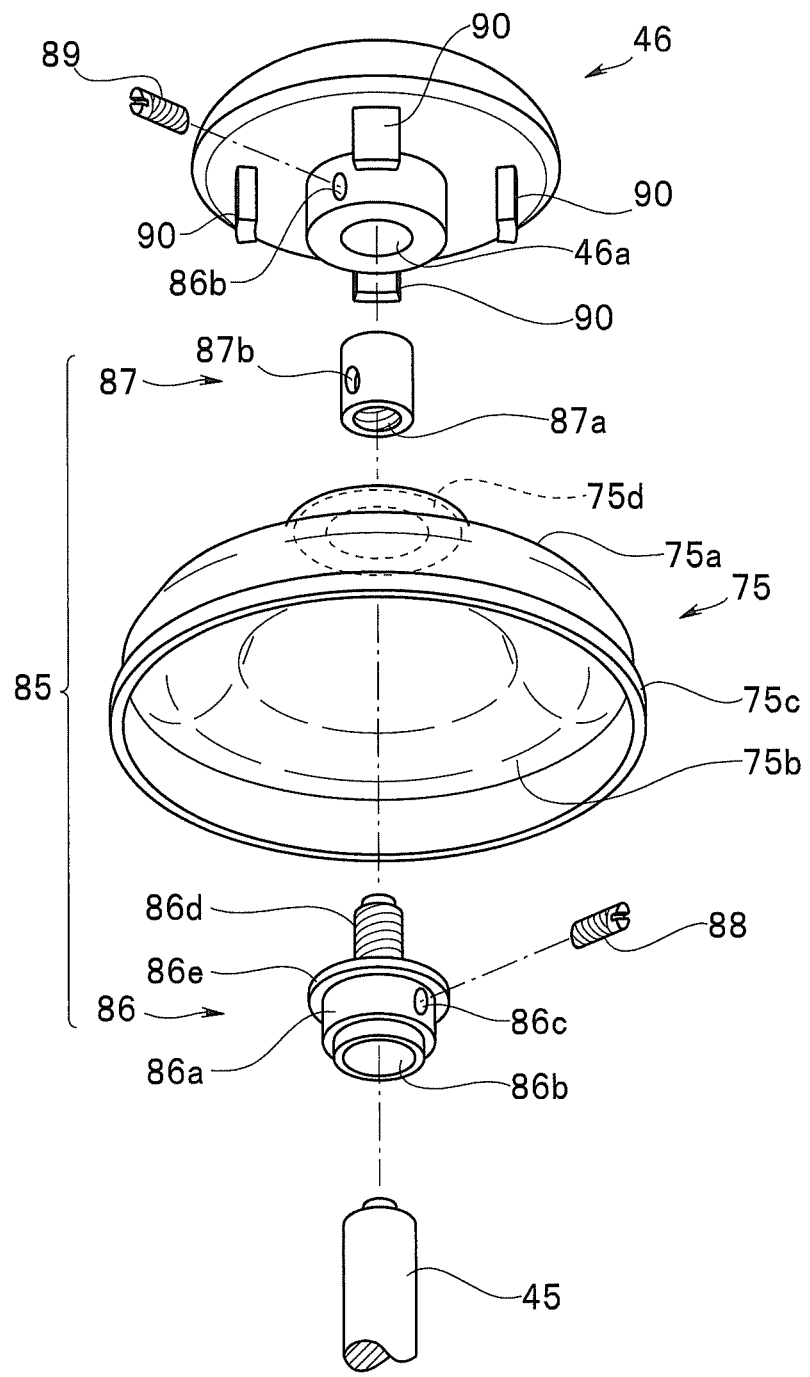
FIG. 4 is an exploded perspective view showing a bending lever and an exterior cover.
Figure 5:
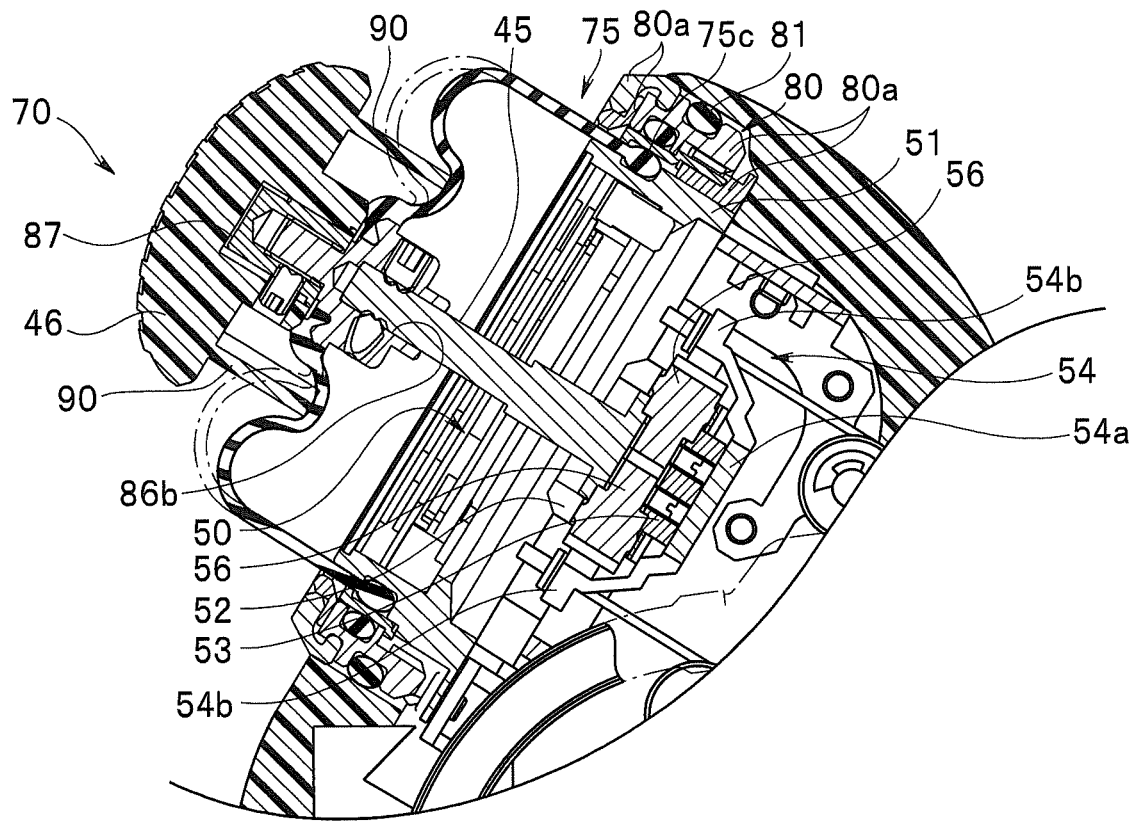
FIG. 5 is a sectional view of a main part showing a state of the exterior cover at the time of applying positive pressure to an inside of the endoscope.
Figure 6:
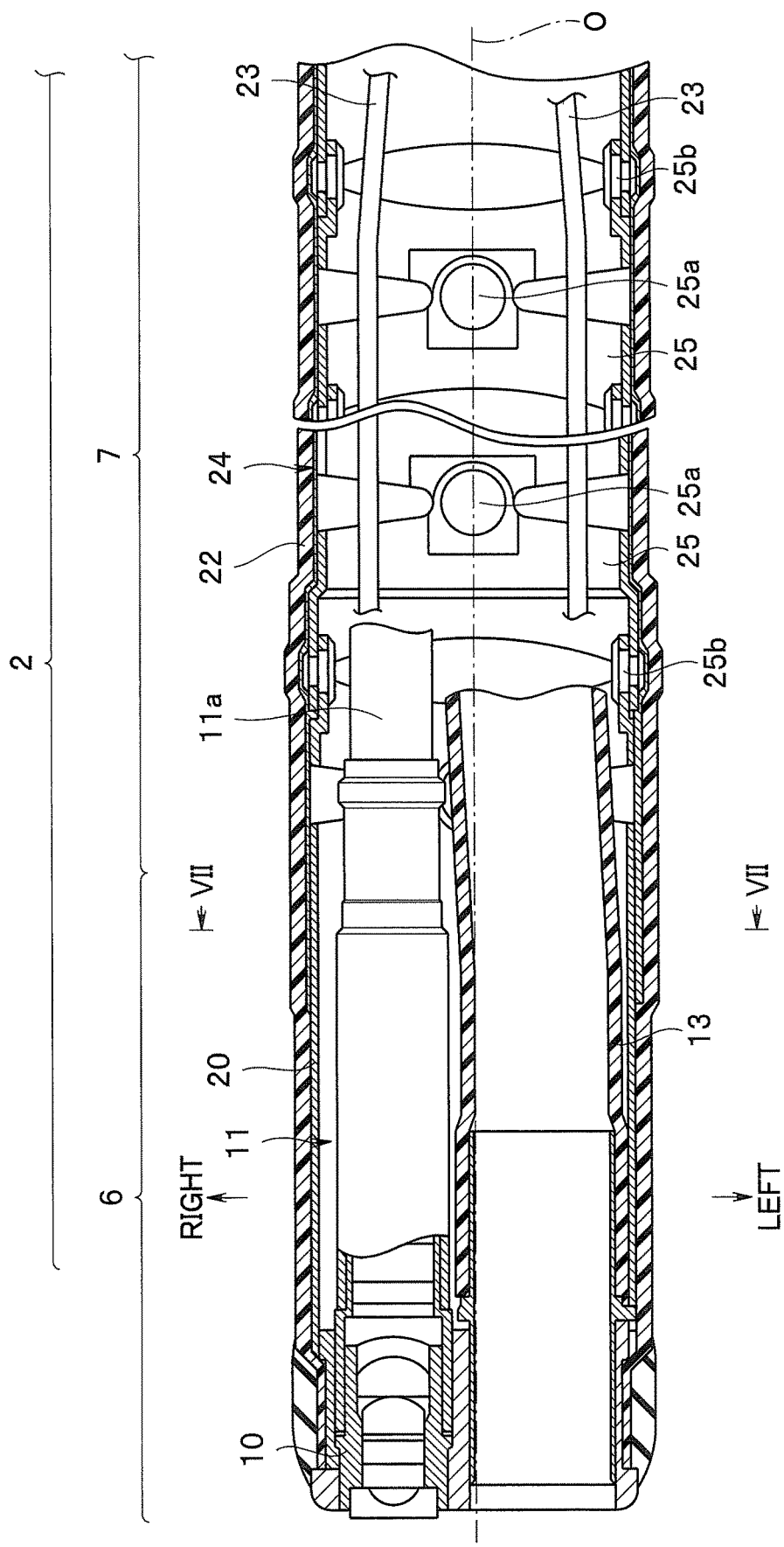
FIG. 6 is a cross-sectional view showing main parts of a distal end portion and a bending portion.
Figure 7:
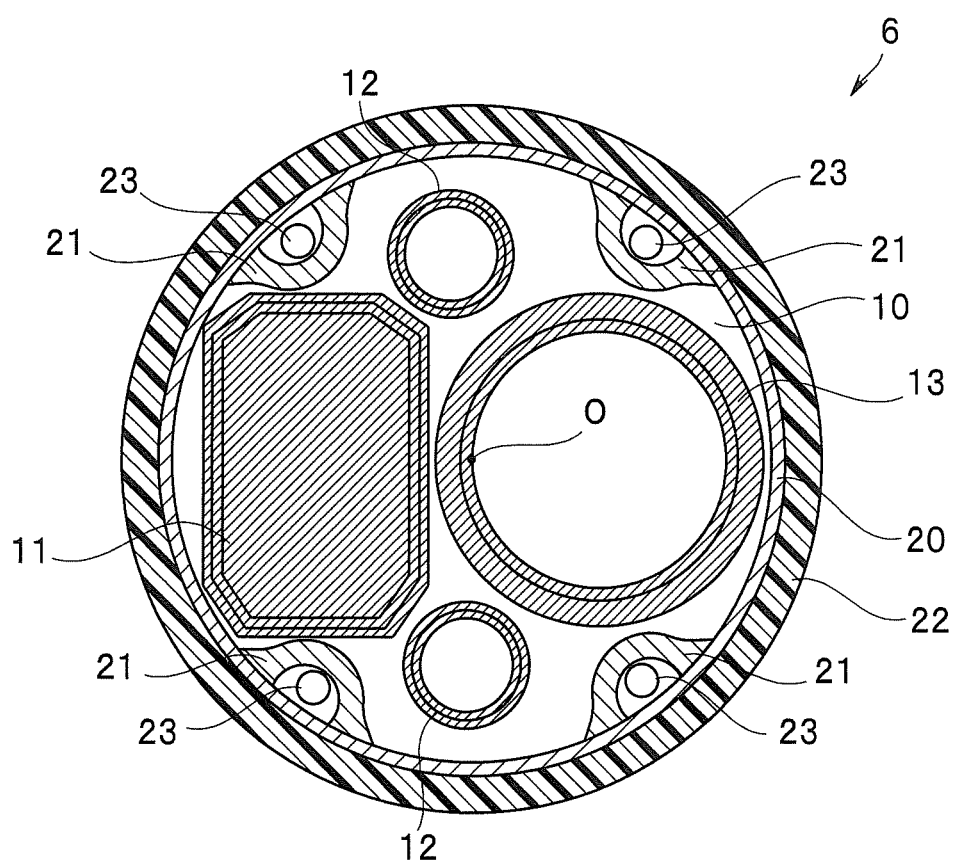
FIG. 7 is a sectional view showing the distal end portion along a VII-VII line in FIG. 6.

An embodiment of the present invention will be described below with reference to drawings. The drawings are according to the embodiment of the present invention. FIG. 1 is a front view showing an external appearance of an endoscope. FIG. 2 is a right side view showing an external appearance of the endoscope. FIG. 3 is a sectional view of a main part of an operation portion. FIG. 4 is an exploded perspective view showing a bending lever and an exterior cover. FIG. 5 is a sectional view of a main part showing a state of the exterior cover at the time of applying positive pressure to an inside of the endoscope. FIG. 6 is a cross-sectional view showing main parts of a distal end portion and a bending portion. FIG. 7 is a sectional view showing the distal end portion along a VII-VII line in FIG. 6.

An endoscope 1 of the present embodiment shown in FIGS. 1 and 2 is a bronchus endoscope, and the endoscope 1 is configured including an insertion portion 2 formed in an elongated tube shape, an operation portion 3 arranged being connected to a proximal end of the insertion portion 2, a universal cord 4 that is an endoscope cable extended from the operation portion 3 and an endoscope connector 5 arranged at a distal end of the universal cord 4.

The insertion portion 2 is configured with a flexible tubular member with a distal end portion 6, a bending portion 7 and a flexible tube portion 8 connectedly arranged in order from a distal end side.

For example, as shown in FIGS. 6 and 7, a distal-end rigid portion 10 made of metal is provided inside the distal end portion 6. In the distal-end rigid portion 10, an image pickup unit 11 internally having an image pickup device such as a CCD or a CMOS, a pair of light guides 12 and a treatment instrument insertion channel 13 are held.

Further, inside the distal end portion 6, a most-distal-end bending piece 20 forming a substantially cylindrical shape is fitted on a proximal end side of the distal-end rigid portion 10, and an outer circumference of the most-distal-end bending piece 20 is covered with a bending rubber 22. On an inner circumference of the most-distal-end bending piece 20, wire fixing portions 21 are provided at four positions around an insertion axis O. At each of the wire fixing portions 21, a distal end of any of four pulling wires 23 inserted in the insertion portion 2 is fixed.

The bending portion 7 is configured so as to positively bend in all directions around the insertion axis O including up-down/right-left directions, in response to an input operation of the operation portion 3 by an operator or the like. That is, the bending portion 7 of the present embodiment is configured including a bending piece set 24 configured with a plurality of bending pieces 25 coupled alternately via pivot portions 25a arranged in the up-down direction of the insertion portion 2 and pivot portions 25b arranged in the right-left direction of the insertion portion 2.

Inside the bending piece set 24, a signal cable 11a extending from the image pickup unit 11, the light guides 12 and the treatment instrument insertion channel 13 are inserted in an arrangement substantially similar to the arrangement in the distal end portion 6. Further, on predetermined bending pieces 25 configuring the bending piece set 24, wire guides (not shown) allowing insertion of the pulling wires 23, respectively, are formed at positions where rotation position around the insertion axis O are substantially similar to rotation positions of the respective wire fixing portions 21 described above. Furthermore, the outer circumference of the bending piece set 24 is covered with the bending rubber 22 extending from the distal end portion 6 side.

The flexible tube portion 8 is configured with a tubular member having flexibility, which is capable of passively bending. Inside the flexible tube portion 8, the signal cable 11a, the light guides 12 and the treatment instrument insertion channel 13, which are described above, are inserted (none of these parts are shown here).

The operation portion 3 is configured including a bend preventing portion 30 connected to the flexible tube portion 8, in a state of covering a proximal end of the flexible tube portion 8, a grasping portion 31 which is arranged being connected to the bend preventing portion 30 and which can be grasped by a hand of a user or the like, and an operation portion body 32 connectedly arranged on a proximal end side of the grasping portion 31. Note that, in the present embodiment, directions around the insertion axis O and the like in the operation portion 3 are defined with a state of the user or the like grasping the grasping portion 31 as a reference. More specifically, front-back and left-right directions (a front face, a back face, left-right side faces and the like) with the user grasping the grasping portion 31 as a reference are defined for the operation portion 3.

As shown in FIG. 1, the grasping portion 31 is formed in a laterally symmetrical shape relative to the insertion axis O (a central axis) so that the user or the like can similarly grasp the grasping portion 31 by either a left hand or a right hand.

Further, on a distal-end-side front face of the grasping portion 31, a treatment instrument insertion portion 35 is provided. The treatment instrument insertion portion 35 is configured including a treatment instrument insertion port 35a through which various treatment instruments (not shown) are inserted. Inside the operation portion 3, the treatment instrument insertion channel 13 communicates with the treatment instrument insertion port 35a via a branching member not shown. Further, a forceps plug (not shown), which is a cover member for blocking the treatment instrument insertion port 35a, is attachable to and detachable from the treatment instrument insertion portion 35.

The operation portion body 32 is configured with a hollow member forming a substantially partially spherical shape expanded mainly leftward, rightward and frontward on the proximal end side of the grasping portion 31. On a front face side of the operation portion body 32, an operation button group 40 for executing various functions of the endoscope 1 is arranged. On a back face side of the operation portion body 32, a bending lever 45 as an operation lever for performing a bending operation of the bending portion 7 is arranged. The universal cord 4 is extended from one side portion (for example, a left side portion) of the operation portion body 32.

Here, a lateral shape of the operation portion body 32 is a shape expanded laterally symmetrically relative to the insertion axis O. In left and right side faces on a distal end side of the operation portion body 32, recess portions for guide 32a configured to guide an index finger or the like of the user grasping the grasping portion 31 to the operation button group 40 are formed respectively.

The universal cord 4 reaches the operation portion 3 from the distal end side through an inside of the insertion portion 2. Furthermore, the universal cord 4 is a composite cable allowing insertion of various signal lines and the like extending from the operation portion 3 inside, allowing insertion of the light guides 12 of a light source device (not shown) and allowing insertion of a tube for air/water feeding extended from an air/water feeding device (not shown).

The endoscope connector 5 is configured including an electrical connector portion 5a to which a signal cable connecting to a video processor (not shown), which is an external apparatus, is connected, on a side face portion and including a light source connector portion 5b to which a light guide and an electrical cable connecting to a light source apparatus (not shown), which is an external apparatus, are connected.

Here, inside the electrical connector portion 5a, a ventilation portion 5c is provided. The ventilation portion 5c communicates with a sealed space 15 formed in an internal space of the endoscope 1 (for example, a series of sealed spaces formed inside the insertion portion 2, the operation portion 3, the universal cord 4 and the endoscope connector 5) (see FIG. 3), and it is possible to introduce positive pressure for a leak test into the sealed space 15 of the endoscope 1 through the ventilation portion 5c.

Next, a configuration of each portion in the operation portion body 32 will be described in more detail.

As shown in FIG. 1, the operation button group 40 is configured including, for example, a suction button 41a projecting from a suction valve 41 detachably fitted to the operation portion body 32, and two button switches 42 to which any function can be assigned from among various functions related to the endoscope 1.

The suction button 41a and the button switches 42 are arranged on the front face side of the operation portion body 32 in a manner of being laterally symmetrical. That is, in the present embodiment, the suction button 41a is arranged at a center of a left and right width of the operation portion body 32 so as to overlap with the insertion axis O. Further, the two button switches 42 are arranged at laterally symmetrical positions with the insertion axis O sandwiched between the suction button switches 42, on a distal end side of the suction button 41a.

Here, as shown in FIG. 3, inside the operation portion body 32, a cylinder 43 arranged being connected to the suction valve 41 is provided. The cylinder 43 is adapted so that the suction valve 41 can be detachably fitted, and is arranged at the center of the left and right width inside the operation portion body 32 so as to overlap with the insertion axis O, corresponding to the arrangement of the suction button 41a.

The bending lever 45 is configured, for example, with a joystick type lever capable of tilting in all directions including the up-down/right-left directions. The bending lever 45 is arranged at a position of being laterally symmetrical on the back face side of the operation portion body 32. That is, in the present embodiment, the bending lever 45 is arranged at the center of the left and right width of the operation portion body 32 so as to overlap with the insertion axis O.

On a tip portion of the bending lever 45, a finger rest portion 46 capable of causing a thumb or the like of the user or the like to be in contact is provided. As shown in FIG. 3, a wire pulling mechanism 50 is connectedly arranged on a proximal end side of the bending lever 45 inside the operation portion 3, and each of the pulling wires 23 is connected to the wire pulling mechanism 50. The bending lever 45 configures a bending operation device 70 for causing the bending portion 7 to perform a bending operation in an arbitrary direction, together with the wire pulling mechanism 50.

The wire pulling mechanism 50 is configured including a housing 51 forming a substantially cylindrical shape, a rotating frame 52 pivotally supported inside the housing 51 in a manner of being freely rotatable (swingable), a base member 53 pivotally supported inside the rotating frame 52 in a manner of being freely rotatable (swingable), and a wire pulling member 54 fixedly arranged on the base member 53.

The rotating frame 52 is configured, for example, with a frame body forming a substantially rectangular shape and pivotally supported in the housing 51 in a manner of being freely rotatable (swingable) via a pair of screws not shown.

The base member 53 is configured with a member forming a substantially columnar shape. The bending lever 45 is integrally formed on a central axis of the base member 53. The base member 53 is arranged on an inner side of the rotating frame 52 and pivotally supported by the rotating frame 52 in a manner of being freely rotatable (swingable) via a pair of screws 56. Here, the pair of screws 56 pivotally supporting the base member 53 to the rotating frame 52 is orthogonal to a pair of screws pivotally supporting the rotating frame 52 to the housing 51. Thereby, the base member 53 is pivotally supported in the housing 51 in a manner of freely rotating around two orthogonal axes, and the bending lever 45 integrally arranged being integrally connected to the base member 53 can tilt in an arbitrary direction.

The wire pulling member 54 is configured with a plate-shaped member from which arm portions 54b are extended in four mutually different directions. More specifically, in the present embodiment, the wire pulling member 54 is configured with a cross-shaped and plate-shaped member for which an angle formed by mutually adjoining arm portions 54b is set at 90 degrees, and a central portion 54a of the wire pulling member 54 is fixed to the base member 53 by screwing or the like. That is, the bending lever 45 is coupled with the wire pulling member 54 via the base member 53, and, thereby, a distal end side of each arm portions 54b is displaceable in response to a tilting operation of the bending lever 45.

On the distal end side of each arm portion 54b, a proximal end of each pulling wires 23 extending from the insertion portion 2 side is connected.

In the operation portion body 32, pulleys 68 corresponding to the respective pulling wires 23 are provided, and extension directions of the pulling wires 23 are adjusted by the respective corresponding pulleys 68.

By the arm portions 54b extending from the wire pulling mechanism 50 being connected to the proximal ends of the respective pulling wires 23 as described above, the bending operation device 70 can adjust a bending angle of the bending portion 7 in response to a tilting operation of the bending lever 45.

The operation portion 3, in which such a bending operation device 70 is provided, is provided with an exterior cover 75 for forming the series of sealed spaces 15 inside the endoscope 1 by providing watertight sealing around the bending lever 45 projecting outside.

An outer periphery portion of the exterior cover 75 is watertightly fixed to the operation portion 3, and an inner periphery portion of the exterior cover 75 is configured with resin material such as flexible rubber watertightly covering an outer side of the bending lever 45.

To describe the above more specifically, for example, as shown in FIGS. 3 and 4, the exterior cover 75 is configured with a donut-plate-shaped member with ridge folding portions 75a and valley folding portions 75b formed on a midway portion between an outer circumferential side and an inner circumferential side, the midway portion having a meander-shaped section. Further, on circumferential ends on the outer circumferential side and the inner circumferential side of the exterior cover 75, each of an outer-circumferential-side sealing ring 75c and an inner-circumferential-side sealing ring 75d forming a thick bead shape is integrally formed.

Between the sealing rings, the outer-circumferential-side sealing ring 75c is fixed to the operation portion body 32 (the operation portion 3) via an outer-circumferential-side cover holder 80.

In the present embodiment, the outer-circumferential-side cover holder 80 is configured with an annular member on which a plurality of holder rings 80a are arranged being superimposed in multiple layers in a diameter direction.

Among the respective holder rings 80a configuring the outer-circumferential-side cover holder 80, holder rings 80a located on the inner circumferential side are fitted on the housing 51 of the wire pulling mechanism 50. Between the holder rings 80a and the housing 51, the outer-circumferential-side sealing ring 75c is pressure-fixed. Thereby, the outer circumferential side of the exterior cover 75 is kept watertight against the outer-circumferential-side cover holder 80.

The outer circumferential side of the outer-circumferential-side cover holder 80 is fitted in an opening portion of the operation portion body 32 via a sealing member 81.

By the outer-circumferential-side cover holder 80 watertightly holding the exterior cover 75 between the outer-circumferential-side cover holder 80 and the housing 51 being fitted in the operation portion body 32 via the sealing member 81, the outer periphery portion of the exterior cover 75 is watertightly fixed to the operation portion body 32 (the operation portion 3).

As shown in FIGS. 3 and 4, the inner-circumferential-side sealing ring 75d is fixed to the bending lever 45 via an inner-circumferential-side cover holder 85. In the present embodiment, the inner-circumferential-side cover holder 85 is configured including a first holder member 86 and a second holder member 87 and interposed between the bending lever 45 and the finger rest portion 46.

The first holder member 86 includes a lever fitting portion 86a to be fitted to the tip portion of the bending lever 45. The lever fitting portion 86a is provided with a hole portion 86b into which the tip portion of the bending lever 45 can be inserted, and a screw hole 86c communicates with a side portion of the hole portion 86b. A male screw portion 86d is arranged projecting from a distal end of the lever fitting portion 86a, and an outward flange portion 86e is integrally formed on a base portion of the male screw portion 86d.

The first holder member 86 configured as described above is held on the bending lever 45 by the bending lever 45 inserted into the hole portion 86b of the lever fitting portion 86a. Pulling-out of the bending lever 45 is prevented by a worm screw 88 screwed in the screw hole 86c. The male screw portion 86d is inserted inside of the inner-circumferential-side sealing ring 75d of the exterior cover 75.

The second holder member 87 is configured with a member forming a substantially columnar shape insertable into a hole portion 46a made in the finger rest portion 46. On a proximal end side of the second holder member 87, a female screw portion 87a to be screwed with the male screw portion 86d of the first holder member 86 is provided. Further, on a side portion of the second holder member 87, a through hole 46b drilled in a side portion of the finger rest portion 46 and a screw hole 87b communicating with the female screw portion 87a are provided.

The second holder member 87 configured as described above is held by the finger rest portion 46 by being inserted in the hole portion 46a of the finger rest portion 46 and a worm screw 89 inserted into the through hole 46b being screwed in the screw hole 87b.

Further, the male screw portion 86d of the first holder member 86 is screwed with the female screw portion 87a of the second holder member 87. The screwing of the male screw portion 86d with the female screw portion 87a is performed up to a position where a bottom face of the finger rest portion 46 causes the inner-circumferential-side sealing ring 75d of the exterior cover 75 to be watertightly fixed by pressure between the bottom face of the finger rest portion 46 and the outward flange portion 86e, and, thereby, the outer side of the bending lever 45 is watertightly covered with the exterior cover 75. Note that the screwed state between the male screw portion 86d and the female screw portion 87a is maintained by the worm screw 89 screwed in the screw hole 87b of the second holder member 87 being fastened and engaged with the male screw portion 86d.

For the exterior cover 75, which provides watertight sealing around the bending lever 45 to form the sealed space 15 inside the endoscope 1, restricting members 90 for restricting expansion due to elastic deformation when internal pressure in the sealed space 15 becomes positive pressure are provided facing the exterior cover 75.

As shown in FIGS. 3 and 4, the restricting members 90 of the present embodiment are configured with a plurality of (for example, four) projecting members integrally formed on a back face side of the finger rest portion 46.

Here, it is desirable that the restricting members 90 are set as long as possible, for example, within a range not hindering a tilting operation of the bending lever 45. Therefore, the restricting members 90 of the present embodiment are set, for example, to a length that does not interfere with the outer-circumferential-side cover holder 80 and the like when the bending lever 45 is tilted and is capable of restricting deformation, as far as possible, of the exterior cover 75 due to expansion.

According to such a configuration, for example, as shown in FIG. 5, a part of expansion of the exterior cover 75 is restricted by the restricting members 90 even when positive pressure is introduced into the sealed space 15 from the ventilation portion 5c and the like at the time of cleaning or the like of the endoscope 1. Thereby, the exterior cover 75 is restricted from expanding up to an expanded shape that is stable relative to restoration force of the exterior cover 75 (for example, an expanded shape as indicated by dash-dotted lines in FIG. 5). Thereby, restoration force urging the exterior cover 75 to an inner side is left in the exterior cover 75, and the exterior cover 75 is promptly restored to an original shape after the internal pressure in the sealed space 15 is released.

According to such an embodiment, by providing the bending lever type (joystick type) endoscope 1, which includes the bending lever 45 capable of adjusting a bending angle of the bending portion 7 in response to a tilting operation of the operation portion 3, and the exterior cover 75 the outer periphery portion of which is watertightly fixed to the operation portion body 32 (the operation portion 3), and the inner periphery portion of which watertightly covers an outer circumference of the bending lever 45, the exterior cover 75 being capable of deforming by pressure fluctuation inside the operation portion 3 (that is, pressure fluctuation of the sealed space 15 formed inside the endoscope 1), with the restricting member 90 configured to restrict expansion of the exterior cover 75 by the fluctuation of the internal pressure, it is possible to cause the exterior cover 75 to be promptly restored to the original shape at the time of having released positive pressure applied to the inside of the endoscope 1.

Thereby, for example, when a leak test is performed in parallel with cleaning of the endoscope 1 and the like, the exterior cover 75 can be promptly restored to the original shape at the time of having released positive pressure applied to the inside of the sealed space 15, and it is possible to prevent occurrence of an air lock and the like and appropriately perform cleaning, disinfection and the like of the endoscope 1.

In this case, by integrally forming the restricting members 90 on the finger rest portion 46 provided on the tip portion of the bending lever 45, it is possible to realize restoration of the exterior cover 75 which has been expanded, without adding new parts and the like.

Figure 8:
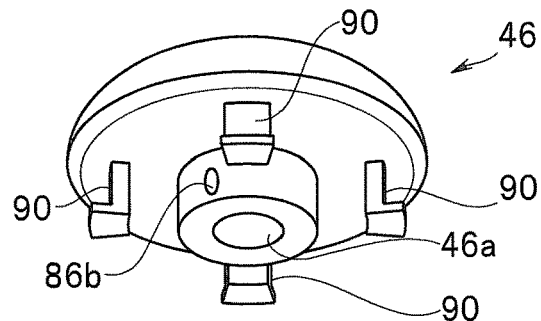
FIG. 8 is a perspective view when a finger rest portion is seen obliquely from below, according to a first modification.

Here, for example, as shown in FIG. 8, a distal end of each of the restricting members 90 configured with the plurality of projecting members can be formed being folded in an L shape. By making such a configuration, it is possible to sufficiently secure contact area at the time when each restricting member 90 restricts expansion of the exterior cover 75. Thereby, it is possible to relax concentration of stress on the exterior cover 75 to effectively suppress breakage and the like of the exterior cover 75.

Figure 9:
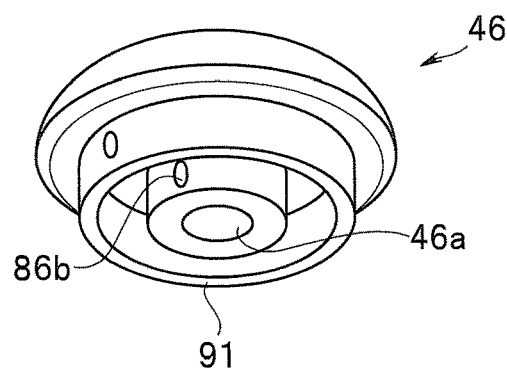
FIG. 9 is a perspective view when the finger rest portion is seen obliquely from below, according to a second modification.

As shown in FIG. 9, for example, it is also possible to, instead of the restricting members 90 configured with the plurality of projecting members, integrally form a restricting member 91 configured with a ring-shaped projecting member on the finger rest portion 46 and arrange the restricting member 91 to face the exterior cover 75. By making such a configuration, it is possible to secure sufficient contact area at the time when the restricting member 91 restricts expansion of the exterior cover 75. Thereby, it is possible to relax concentration of stress on the exterior cover 75 to effectively suppress breakage and the like of the exterior cover 75.

Figure 10:
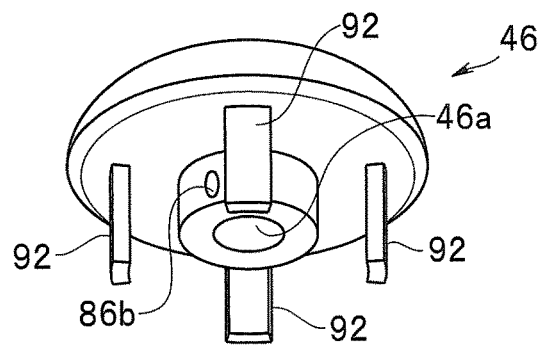
FIG. 10 is a perspective view when the finger rest portion is seen obliquely from below, according to a third modification.

As shown in FIG. 10, for example, it is also possible to configure respective restricting members 92 with a plurality of projecting members having predetermined elasticity. By making such a configuration, it is possible to, for example, even when the restricting members 92 are extended to a position where the restricting members 92 interfere with the outer-circumferential-side cover holder 80 and the like when the bending lever 45 tilts, sufficiently ensure a tilting operation of the bending lever 45 by elastic deformation of the restricting members 92. In this case, it is desirable that hardness of each restricting member 92 is set higher than hardness of the exterior cover 75 in order to appropriately restore the exterior cover 75.

Figure 11:
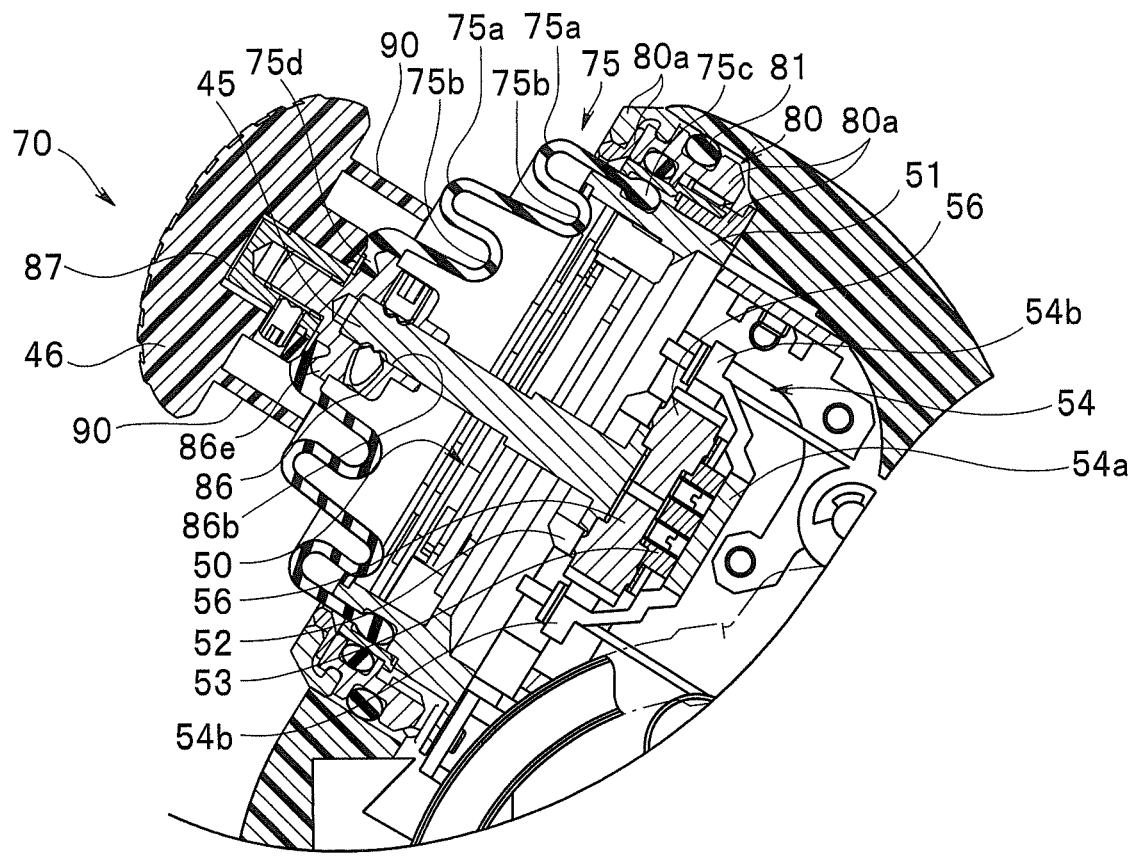
FIG. 11 is a sectional-view of a main part of the operation portion according to a fourth modification.

Further, for example, as shown in FIG. 11, the exterior cover 75 may be configured with the donut-plate-shaped member with the ridge folding portions 75a and the valley folding portions 75b formed on a midway portion, the midway portion having a meander-shaped section. In such a configuration, it is also possible to, by restricting a part of expansion of the exterior cover 75 by the restricting members 90, appropriately restore the exterior cover 75 to the original shape at the time of having released positive pressure.

Note that the present invention is not limited to the embodiment described above, and various modifications and changes are possible. The various modifications and changes are also within the technical scope of the present invention. For example, it is a matter of course that components of the embodiment and the respective modifications described above may be appropriately combined.

What is claimed is:

1. An endoscope comprising:
   an operation portion;
   an exterior cover configured to seal an opening in the operation portion, the operation portion having a sealed space bound by the exterior cover and the operation portion, the exterior cover being configured to deform in response to a change in internal pressure in the sealed space;
   an operation lever watertightly fixed to the exterior cover, the operation lever extending along a longitudinal axis from a distal end thereof to a proximal end thereof, the proximal end of the operation lever disposed within the operation portion; and
   one or more restricting projections provided on the operation lever so as to extend toward the proximal end of the operation lever, the one or more restricting projections being configured to restrict expansion of the exterior cover resulting from the change in the internal pressure.

2. The endoscope according to claim 1, wherein the one or more restricting projections are integrally formed on a finger rest portion provided on the distal end of the operation lever.

3. The endoscope according to claim 1, wherein the one or more restricting projections comprise a plurality of restricting projections each arranged to extend towards the proximal end of the operation lever.

4. The endoscope according to claim 1, wherein a distal end portion of the one or more restricting projections comprises an extension extending radially from the longitudinal axis of the operation lever.

5. The endoscope according to claim 1, wherein the one or more restricting projections comprises a ring-shaped projection arranged to extend towards the proximal end of the operation lever.

6. The endoscope according to claim 1, wherein the one or more restricting projections is configured with an elastic body having a hardness higher than a hardness of the exterior cover.

* * * * *